United States Patent
Widdowson et al.

(10) Patent No.: US 6,767,922 B2
(45) Date of Patent: Jul. 27, 2004

(54) IL-8 RECEPTOR ANTAGONISTS

(75) Inventors: Katherine Louisa Widdowson, King of Prussia, PA (US); Qi Jin, King of Prussia, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/220,967

(22) PCT Filed: Mar. 14, 2001

(86) PCT No.: PCT/US01/08187

§ 371 (c)(1),
(2), (4) Date: Sep. 6, 2002

(87) PCT Pub. No.: WO01/68570

PCT Pub. Date: Sep. 20, 2001

(65) Prior Publication Data

US 2003/0065188 A1 Apr. 3, 2003

Related U.S. Application Data

(60) Provisional application No. 60/189,175, filed on Mar. 14, 2000.

(51) Int. Cl.[7] .................. A61K 31/275; A61K 31/24; A61K 31/22; A61K 31/195; A61K 31/17
(52) U.S. Cl. .................. 514/522; 514/534; 514/546; 514/562; 514/597; 558/411; 560/13; 560/251; 562/430; 564/49

(58) Field of Search .................. 514/522, 534, 514/546, 562, 597; 558/411; 560/13; 562/430; 564/49

(56) References Cited

FOREIGN PATENT DOCUMENTS

| WO | WO 97 49680 | 12/1997 |
| WO | WO 97 49286 | 12/2001 |

OTHER PUBLICATIONS

Kalcheva, V., et al., "Synthesis of 1–(2–hydroxyaryl)–and 1–methyl–1–(2–hydrozyaryl)–3–n–butylureas."Izv. Khim. 1988, 21(1), 101–5 (Bulgarian).

Database CAPLUS on STN, An 1992:426229, Chem. abstr., vol. 117, 1992, (Columbus, OH, USA), Lozanova, KH. S. et al., "Synthesis and Biological Activity of 1–(2–hydroxyaryl)–3–benzyl– and 1–(2–hydroxyaryl)–3–pyrrolidinylureas." Dok. Bulg. Akad. Nauk. 1991, 44(11), 45–8 (English).

*Primary Examiner*—Peter O'Sullivan
(74) *Attorney, Agent, or Firm*—Soma G. Simon; Mary E. McCarthy; Charles M. Kinzig

(57) ABSTRACT

This invention relates to novel compounds of Formula (I) to (VII), and compositions thereof, useful in the treatment of disease states mediated by the chemokine, Interleukin-8 (IL-8).

13 Claims, No Drawings

IL-8 RECEPTOR ANTAGONISTS

This is a 371 of International Application PCT/US01/08187, filed 14 Mar. 2001, which claims benefit from the following Provisional Application: 60/189,175, filed 14 Mar. 2000.

FIELD OF THE INVENTION

This invention relates to novel sulfonamide substituted diphenyl urea compounds, pharmaceutical compositions, processes for their preparation, and use thereof in treating IL-8, GROα, GROβ, GROγ, NAP-2, and ENA-78 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al., *J. Clin. Invest.* 84, 1045 (1989); J. Schroder et al, *J. Immunol.* 139, 3474 (1987) and *J. Immunol.* 144, 2223 (1990); Strieter, et al., *Science* 243, 1467 (1989) and *J. Biol. Chem.* 264, 10621 (1989); Cassatella et al., *J. Immunol.* 148, 3216 (1992).

GROα, GROβ, GROγ and NAP-2 also belong to the chemokine family. Like IL-8 these chemokines have also been referred to by different names. For instance GROα, β, γ have been referred to as MGSAα, β and γ respectively (Melanoma Growth Stimulating Activity), see Richmond et al., *J. Cell Physiology* 129, 375 (1986) and Chang et al., *J. Immunol* 148, 451 (1992). All of the chemokines of the α-family which possess the ELR motif directly preceding the CXC motif bind to the IL-8 B receptor (CXCR2).

IL-8, GROα, GROβ, GROγ, NAP-2, and ENA-78 stimulate a number of functions in vitro. They have all been shown to have chemoattractant properties for neutrophils, while IL-8 and GROα have demonstrated T-lymphocytes, and basophilic chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al., *FEBS Lett.* 307, 97 (1992); Miller et al., *Crit. Rev. Immunol.* 12, 17 (1992); Oppenheim et al., *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis, Strieter et al., *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the IL-8β receptor (CXCR2). Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GROα, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds, which are capable of binding to the IL-8α at or β receptor. Therefore, conditions associated with an increase in IL-8 production (which is responsible for chemotaxis of neutrophil and T-cells subsets into the inflammatory site) would benefit by compounds, which are inhibitors of IL-8 receptor binding.

SUMMARY OF THE INVENTION

This invention provides for a method of treating a chemokine mediated disease, wherein the chemokine is one which binds to an IL-8 a or b receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

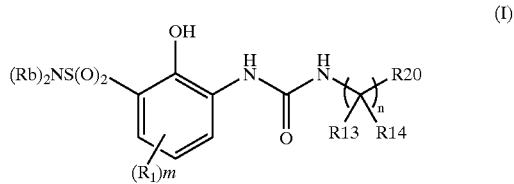

wherein $R_b$ is independently selected from the group consisting of hydrogen, $NR_6R_7$, OH, $OR_a$, $C_{1-5}$alkyl, aryl, aryl$C_{1-4}$alkyl, aryl $C_{2-4}$alkeny,; cycloalkyl, cycloalkyl $C_{1-5}$alkyl, heteroaryl, heteroaryl$C_{1-4}$alkyl, heteroaryl$C_{2-4}$alkenyl, heterocyclic, heterocyclic $C_{1-4}$alkyl, and a heterocyclic $C_{2-4}$alkenyl moiety, all of which moieties may be optionally substituted one to three times independently by halogen, nitro, halosubstituted $C_{1-4}$ alkyl, $C_{1-4}$ alkyl, amino, mono or di-$C_{1-4}$ alkyl substituted amine, $OR_a$, $C(O)R_a$, $NR_aC(O)OR_a$, $OC(O)NR_6R_7$, hydroxy, $NR_9C(O)R_a$, $S(O)_{m'}R_a$, $C(O)NR_6R_7$, $C(O)$ OH, C(O)OR$_a$, S(O)$_2$NR$_6$R$_7$, and NHS(O)$_2$R$_a$, alternatively, the two R$_b$ substituents can join to form a 3–10 membered ring, optionally substituted and containing, in addition to carbon, independently, 1 to 3 moieties selected from the group consisting of NR$_a$, O, S, SO, and SO$_2$, which can be optionally unsaturated;

R$_a$ is selected from the group consisting of alkyl, aryl, arylC$_{1-4}$alkyl, heteroaryl, heteroaryl C$_{1-4}$alkyl, heterocyclic, COOR$_a$, and a heterocyclic C$_{1-4}$alkyl moiety, all of which moieties may be optionally substituted;

m is an integer having a value of 1 to 3;

m' is 0, or an integer having a value of 1 or 2;

n is an integer having a value of 1 to 5;

q is 0, or an integer having a value of 1 to 10;

t is 0, or an integer having a value of 1 or 2;

s is an integer having a value of 1 to 3;

R$_1$ is independently selected from the group consisting of hydrogen, halogen, nitro, cyano, C$_{1-10}$ alkyl, halosubstituted C$_{1-10}$ alkyl, C$_{2-10}$ alkenyl, C$_{1-10}$ alkoxy, halosubstituted C$_{1-10}$alkoxy, azide, S(O)$_t$R$_4$, (CR$_8$R$_8$)$_q$ S(O)$_t$R$_4$, hydroxy, hydroxy substituted C$_{1-4}$alkyl, aryl, aryl C$_{1-4}$ alkyl, aryl C$_{2-10}$ alkenyl, aryloxy, aryl C$_{1-4}$ alkyloxy, heteroaryl, heteroarylalkyl, heteroaryl C$_{2-10}$ alkenyl, heteroaryl C$_{1-4}$ alkyloxy, heterocyclic, heterocyclic C$_{1-4}$alkyl, heterocyclicC$_{1-4}$alkyloxy, heterocyclicC$_{2-10}$ alkenyl, (CR$_8$R$_8$)$_q$ NR$_4$R$_5$, (CR$_8$R$_8$)$_q$ C(O)NR$_4$R$_5$, C$_{2-10}$ alkenyl C(O)NR$_4$R$_5$, (CR$_8$R$_8$)$_q$ C(O)NR$_4$R$_{10}$, S(O)$_3$R$_8$, (CR$_8$R$_8$)$_q$ C(O)R$_{11}$, C$_{2-10}$ alkenyl C(O)R$_{11}$, C$_{2-10}$ alkenyl C(O)OR$_{11}$, (CR$_8$R$_8$)$_q$ C(O)OR$_{11}$, (CR$_8$R$_8$)$_q$ OC(O)R$_{11}$, (CR$_8$R$_8$)$_q$NR$_4$C(O)R$_{11}$, (CR$_8$R$_8$)$_q$ C(NR$_4$)NR$_4$R$_5$, (CR$_8$R$_8$)$_q$ NR$_4$C(NR$_5$)R$_{11}$, (CR$_8$R$_8$)$_q$ NHS(O)$_2$R$_a$, and (CR$_8$R$_8$)$_q$ S(O)$_2$NR$_4$R$_5$; or two R$_1$ moieties together may form O—(CH$_2$)$_s$O or a 5 to 6 membered saturated or unsaturated ring, wherein the alkyl, aryl, arylalkyl, heteroaryl, heterocyclic moieties may be optionally substituted;

R$_4$ and R$_5$ are, independently, selected form the group consisting of hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, and heterocyclicC$_{1-4}$ alkyl; or R$_4$ and R$_5$ together with the nitrogen to which they are attached form a 5 to 7 member ring which may optionally comprise an additional heteroatom selected from O, N and S;

R$_6$ and R$_7$ are independently selected from the group consisting of hydrogen, C$_{1-4}$ alkyl, heteroaryl, aryl, aklyl aryl, and alkyl$_{1-4}$ heteroalkyl; or R$_6$ and R$_7$ together with the nitrogen to which they are attached form a 5 to 7 member ring which ring may optionally contain an additional heteroatom is selected from oxygen, nitrogen and sulfur, which ring may be optionally substituted;

R$_8$ is hydrogen or C$_{1-4}$ alkyl;

R$_9$ is a C$_{1-4}$ alkyl;

R$_{10}$ is C$_{1-10}$ alkyl C(O)$_2$R$_8$;

R$_{11}$ is selected from the group consisting of hydrogen, optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, and optionally substituted heterocyclicC$_{1-4}$alkyl; and R$_{13}$ and R$_{14}$ are independently selected from the group consisting of hydrogen, optionally substituted C$_{1-4}$ alkyl, optionally substituted C$_{1-4}$ alkynyl, optionally substituted C$_{1-4}$ alkenyl optionally substituted heteroaryl, optionally substituted heteroarylC$_{1-4}$ alkyl, optionally substituted heterocyclic, optionally substituted heterocyclicC$_{1-4}$alkyl, halogen, nitro, OR$_a$, NR$_6$R$_7$, C(O)R$_a$, NR$_{11}$C(O)OR$_a$, OC(O)NR$_6$R$_7$, NR$_{11}$C(O)R$_a$, S(O)$_m$R$_a$, C(O)NR$_6$R$_7$, C(O)OH, C(O)OR$_a$, S(O)$_2$NR$_6$R$_7$, and NR$_{11}$S(O)$_2$R$_a$; and R$_{20}$ is selected from the group consisting of hydrogen, alkyl, alkynyl, alkenyl, heterocyclic, and heteroaromatic all of which maybe optionally substituted;

or a pharmaceutically acceptable salt thereof.

DETAILED DESCRIPTION OF THE INVENTION

The compounds of Formula (I), may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

Suitably, R$_b$ is independently hydrogen, NR$_6$R$_7$, OH, OR$_a$, C$_{1-4}$alkyl, aryl, arylC$_{1-4}$alkyl, aryl C$_{2-4}$alkenyl, heteroaryl, heteroarylC$_{1-4}$alkyl, heteroarylC$_{2-4}$ alkenyl, heterocyclic, heterocyclic C$_{1-4}$alkyl, or a heterocyclic C$_{2-4}$alkenyl moiety, all of which moieties may be optionally substituted one to three times independently by halogen, nitro, halosubstituted C$_{1-4}$ alkyl, C$_{1-4}$ alkyl, amino, mono or di-C$_{1-4}$ alkyl substituted amine, cycloalkyl, cycloalkyl C$_{1-5}$ alkyl, OR$_a$, C(O)R$_a$, NR$_a$C(O)OR$_a$, OC(O)NR$_6$R$_7$, aryloxy, aryl C$_{1-4}$ oxy, hydroxy, C$_{1-4}$ alkoxy, NR$_9$C(O)R$_a$, S(O)$_m$R$_a$, C(O)NR$_6$R$_7$, C(O)OH, C(O)OR$_a$, S(O)$_2$NR$_6$R$_7$, NHS(O)$_2$R$_a$. Alternatively, the two R$_b$ substituents can join to form a 3–10 membered ring, optionally substituted and containing, in addition to carbon, independently, 1 to 3 NR$_9$, O, S, SO, or SO$_2$ moities which can be optionally substituted.

Suitably, R$_a$ is an alkyl, aryl, arylC$_{1-4}$alkyl, heteroaryl, heteroaryl C$_{1-4}$alkyl, heterocyclic, or a heterocyclic C$_{1-4}$alkyl moiety, all of which moieties may be optionally substituted.

Suitably, R$_1$ is independently selected from hydrogen; halogen; nitro; cyano; halosubstituted C$_{1-10}$ alkyl, such as CF$_3$, C$_{1-10}$ alkyl, such as methyl, ethyl, isopropyl, or n-propyl, C$_{2-10}$ alkenyl, C$_{1-10}$ alkoxy, such as methoxy, or ethoxy; halosubstituted C$_{1-10}$ alkoxy, such as trifluoromethoxy, azide, (CR$_8$R$_8$)$_q$ S(O)$_t$R$_4$, wherein t is 0, 1 or 2, hydroxy, hydroxy C$_{1-4}$alkyl, such as methanol or ethanol, aryl, such as phenyl or naphthyl, aryl C$_{1-4}$ alkyl, such as benzyl, aryloxy, such as phenoxy, aryl C$_{1-4}$ alkyloxy, such as benzyloxy; heteroaryl, heteroarylalkyl, heteroaryl C$_{1-4}$ alkyloxy; aryl C$_{2-10}$ alkenyl, heteroaryl C$_{2-10}$ alkenyl, heterocyclic C$_{2-10}$ alkenyl, (CR$_8$R$_8$)$_q$NR$_4$R$_5$, C$_{2-10}$ alkenyl C(O)NR$_4$R$_5$, (CR$_8$R$_8$)$_q$C(O)NR$_4$R$_5$, (CR$_8$R$_8$)$_q$C(O)NR$_4$R$_{10}$, S(O)$_3$H, S(O)$_3$R$_8$, (CR$_8$R$_8$)$_q$C(O)R$_{11}$, C$_{2-10}$ alkenyl C(O) R$_{11}$, C$_{2-10}$ alkenyl C(O)OR$_{11}$, (CR$_8$R$_8$)$_q$ C(O) R$_{11}$, (CR$_8$R$_8$)$_q$ C(O)O R$_{11}$, (CR$_8$R$_8$)$_q$ OC(O)R$_{11}$, (CR$_8$R$_8$)$_q$NR$_4$C(O)R$_{11}$, (CR$_8$R$_8$)$_q$C(NR$_4$)NR$_4$R$_5$, (CR$_8$R$_8$)$_q$ NR$_4$C(NR$_5$)R$_{11}$, (CR$_8$R$_8$)$_q$NHS(O)$_2$R$_a$, (CR$_8$R$_8$)$_q$S(O)$_2$NR$_4$R$_5$. All of the aryl, heteroaryl, and heterocyclic-containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O, N and S.

Suitably, $R_8$ is independently hydrogen or $C_{1-4}$ alkyl.

Suitably, $R_9$ is hydrogen or a $C_{1-4}$ alkyl;

Suitably, q is 0 or an integer having a value of 1 to 10.

Suitably, $R_{10}$ is $C_{1-10}$ alkyl $C(O)_2R_8$, such as $CH_2C(O)_2H$ or $CH_2C(O)_2CH_3$.

Suitably, $R_{11}$ is hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

Suitably, $R_{12}$ is hydrogen, $C_{1-10}$ alkyl, optionally substituted aryl or optionally substituted arylalkyl.

Suitably, $R_a$ is an alkyl, aryl $C_{1-4}$ alkyl, heteroaryl, heteroaryl-$C_{1-4}$alkyl, heterocyclic, or a heterocyclic$C_{1-4}$ alkyl, wherein all of these moieties may all be optionally substituted.

$R_{13}$ and $R_{14}$ are suitably hydrogen, optionally substituted $C_{1-4}$ alkyl, optionally substituted heteroaryl, optionally substituted heteroaryl$C_{1-4}$ alkyl, optionally substituted heterocyclic, optionally substituted heterocyclic$C_{1-4}$alkyl, halogen, nitro, $OR_a$, $NR_6R_7$, $NR_{11}C(O)OR_a$, $OC(O)NR_6R_7$, $NR_{11}C(O)R_a$, $C(O)NR_6R_7$, $S(O)_2NR_6R_7$, or $NR_{11}S(O)_2R_a$.

$R_{20}$ is suitably $C_{1-4}$ alkyl, alkenyl, heteroaryl, heteroaryl$C_{1-4}$alkyl, heterocyclic, or heterocyclic$C_{1-4}$alkyl all of which may be optionally substituted.

As used herein, "optionally substituted" unless specifically defined shall mean such groups as halogen, such as fluorine, chlorine, bromine or iodine, hydroxy; hydroxy substituted $C_{1-10}$alkyl, $C_{1-10}$ alkoxy, such as methoxy or ethoxy, $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_4R_5$ group, $NHC(O)R_{11}$, $C(O)NR_8R_{11}$, $C(O)OH$, $S(O)_2NR_8R_{11}$, NHS$(O)_2R_9$, $C_{1-10}$ alkyl, such as methyl, ethyl, propyl, isopropyl, or t-butyl, halosubstituted $C_{1-10}$ alkyl, such $CF_3$, an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl, $C_{1-10}$ alkoxy; $S(O)_{m'}C_{1-10}$ alkyl; amino, mono & di-substituted alkyl amino, such as in the $NR_4R_5$ group; $C_{1-10}$ alkyl, or halosubstituted $C_{1-10}$ alkyl, such as $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized $S(O)_2$ moiety.

"wherein two $R_1$ moieties may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative compounds of Formula (I) include:

N-allyl-N'-(3-aminosulfonyl-4-chloro-2-hydroxyphenyl) urea;

N-(3-aminosulfonyl-4-chloro-2-hydroxyphenyl)-N'-isopropylurea;

N-(3-aminosulfonyl-4-chloro-2-hydroxyphenyl)-N'-ethylurea;

N-(3-aminosulfonyl-4-chloro-2-hydroxyphenyl)-N'-propylurea;

N-(3-aminosulfonyl-4-chloro-2-hydroxyphenyl)-N'-(ethoxycarbonyl)methylurea;

6-Chloro-2-hydroxy-3-(3-phenethyl-ureido)-benzenesulfonamide;

3-(3-sec-Butyl-ureido)-6-chloro-2-hydroxy-benzenesulfonamide;

6-Chloro-3-[3-(1-ethyl-propyl)-ureido]-2-hydroxy-benzenesulfonamide;

6-Chloro-2-hydroxy-3-[3-(1-methyl-butyl)-ureido]-benzenesulfonamide;

(2S,3S)-2-[3-(4-Chloro-2-hydroxy-3-sulfamoyl-phenyl)-ureido]-3-methyl-pentanoic acid methyl ester;

(S)-2-[3-(4-Chloro-2-hydroxy-3-sulfamoyl-phenyl)-ureido]-3-methyl-pentanoic acid.

METHODS OF PREPARATION

The compounds of Formulas (I) may be obtained by applying synthetic procedures, some of which are illustrated in the Schemes below. The synthesis provided for in these Schemes is applicable for the producing compounds of Formulas (I), having a variety of different R, $R_b$, and $R_{20}$ groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art.

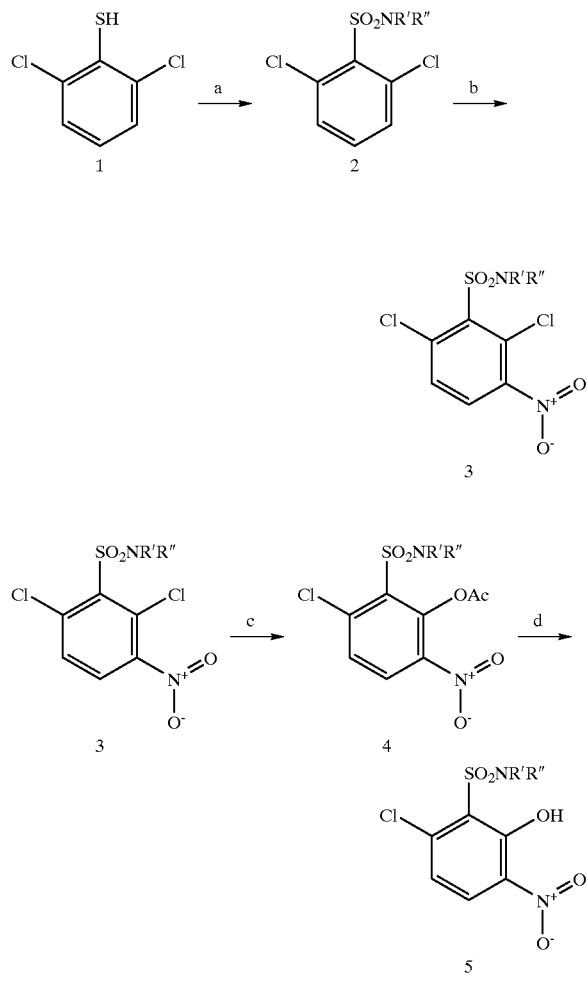

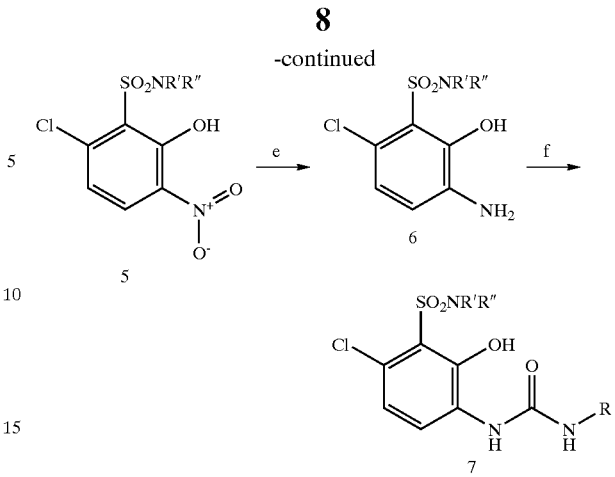

a) i) NCS, AcOH, $H_2O$, ii NR'R"H, pyr b) $H_2SO_4$, $HNO_3$
c) NaOAc, 18-crown-6
d) $H_2SO_4$, MeOH e) Pd/C, $H_2$ f) RCNO, DMF The desired 4-chloro N-(3-sulfonamido-2-hydroxy phenyl)-N"-alkyl urea can synthesized from the commercially available 2,6-dichloro thiophenol using the procedure elaborated above in Scheme 1. The thiol can be oxidized to the corresponding sulfonyl halide using a halogenating agent, such as NCS, NBS, $Cl_2$ or $Br_2$, in the presence of a protic solvent, such as water, acetic acid, or an alcohol or combination. The yield may be increased if a buffering agent, such as sodium or potassium acetate is included in the reaction mixture, and the reaction is conducted at or below room temperature. The corresponding sulfonyl halide can then be condensed with an amine in presence of a base such as pyridine, triethyl amine, potassium carbonate or sodium hydride to form the analogous sulfonamide 2-scheme 1. The dichlorosulfonamide 2-scheme 1 can be nitrated using strong nitrating conditions such as nitric acid in sulfuric acid to form the aromatic nitro compound 3-scheme 1. The chlorine ortho to the nitro group can be selectively hydrolyzed using acetate salt such as sodium acetate in the presence of a crown ether, such as 18-crown-6, to form the acetate 4-scheme 1. The acetate group can be hydrolyzed under acidic conditions in an alcohol solvent such as methanol or ethanol with a catalytic amount of acid to form the phenol 5-scheme 1. The nitro can be reduced by conditions well known in the art such as hydrogen and palladium on carbon, tin chloride in methanol, zinc in acetic acid or thiol to form the corresponding aniline 5-scheme 1. The aniline can then be coupled with a commercially available isocyanate or thioisocyanate to form the desired urea or thio urea. Alternatively the desired isocyanates can be made by condensing the amine with triphosgene in the presence of base (such as potassium carbonate) or by reacting the carboxylic acid with diphenyl phosphoryl azide in the presence of a base (such as triethyl amine).

Scheme 2

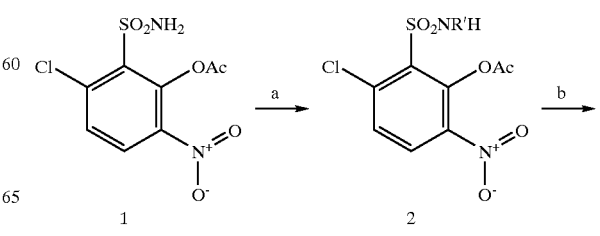

-continued

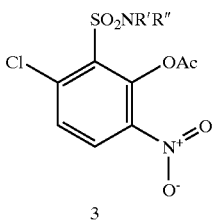

a) NaH, R'X b)NaH R"X

If the sulfonamide 1-scheme 2 (3-scheme 1) is unfunctionalized R'=R"=H then it can be functionalized as required herein, by alkylation. The sulfonamide is deprotonated using a base such as sodium hydride and then alkylated using an alkyl halide such as benzyl bromide or methyl iodide form 2-scheme 2. The sulfonamide can then be alkylated a second time using sodium hydride and another alkyl halide to form 3-scheme 2. This compound can then be converted to the desired urea using the process elaborated in scheme 1.

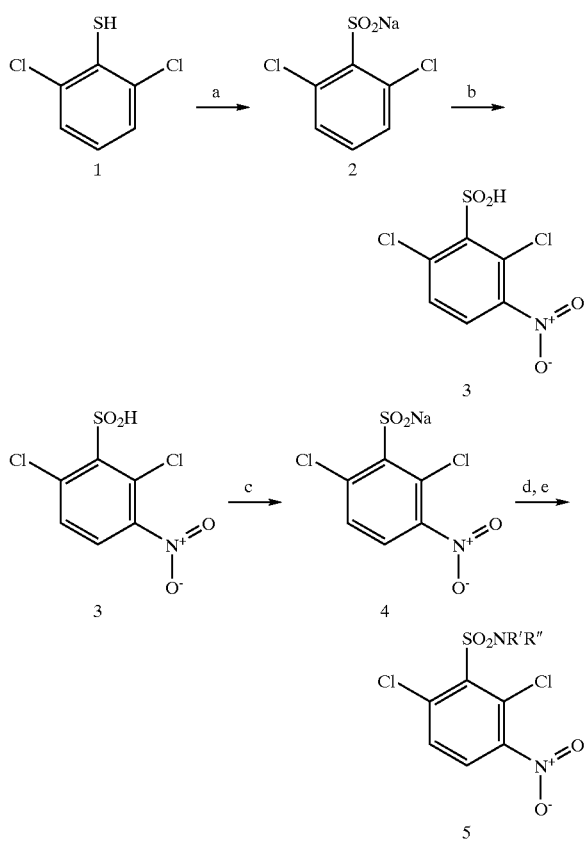

Scheme 3 a)i)NCS, AcOH, $H_2O$ ii)NaOH MeOH b)$H_2SO_4$, $HNO_3$ c)NaOH MeOH d) $PCl_5$, $POCl_3$ e)NHR'R", $Et_3N$

An alternative route to 5-scheme 3 (3-scheme 1) is outlined above, in scheme 3 wherein the commercially available 2,6-dichloro thiol can be oxidized to the sulfonyl halide using a halogenating agent such as NCS, NBS, chlorine or bromine in the presence of a protic solvent such as alcohol, acetic acid or water. The sulfonyl halide can be hydrolyzed by using a metal hydroxide such as sodium or potassium hydroxide to form the corresponding sulfonic acid salt. The sulfonic acid salt can then be nitrated under nitration conditions such as nitric acid in a solvent of strong acid such as sulfuric acid to form the nitro phenyl sulfonic acid 3-scheme 3. The sulfonic acid 3-scheme 3 can be converted to the sulfonamide 5-scheme 3 using a three step procedure involving the formation of the metal salt using a base such as sodium hydroxide, sodium hydride or sodium carbonate to form 4-scheme 3. The sulfonic acid salt is then converted to the sulfonyl chloride using $PCl_5$ with $POCl_3$ as a solvent. The sulfonyl chloride can then be converted to the corresponding sulfonamide using the desired amine HNR'R" in triethyl amine at temperatures ranging from $-78°$ C. to $60°$ C. to form the corresponding sulfonamide 5-scheme 3 (3-scheme 1). The sulfonamide 5-scheme 3 can be further elaborated by the methods contained in scheme 1. This method is not limited to the 2,6-dichloro thiol it can also be applied to the 2,6-difluoro thiol, 2,6-dibromo thiol and the 2,6-diiodo thiol. The halogens in these compounds can be converted to the corresponding cyano, amino, thiol, or alkoxy compounds by nucleophilic displacement reactions using nucleophiles such as alkyl thiolates, alkoxides, amine and cyanides. The halogens can also be further functionalized by palladium coupling and carbonylation reactions, well known in the art, to form the corresponding amido, carbonyl, alkenyl, alkyl, phenyl and heterocyclic substituted products as required by Formula (I).

SYNTHETIC EXAMPLES

The invention will now be described by reference to the following examples, which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

General Synthesis of 2-hydroxy-3-amino-6-chlorobenzenesulfonamide a) 2,6-dichlorobenzenesulfonyl chloride Into a mixture of 200 milliliters (hereinafter "mL") of acetic acid, water and dichloromethane (3/1/4, v/v/v), 2,6-dichlorobenzenethiol (10.0 grams (hereinafter "g"), 55.8 millimoles (hereinafter "mmol"), N-chlorosuccinimide (37.28 g, 279 mmol) and potassium acetate (2.29 g, 27.9 mmol) were added. The resulting mixture was stirred at 0° C., then warmed to room temperature overnight. The mixture was then diluted with 200 mL of dichloromethane, and washed with water (100 mL×3). The organic layer was dried ($Na_2SO_4$) and concentrated to give the desired product (11 g, 80%). $^1$H NMR ($CDCl_3$):δ7.57 (d, 2H), 7.47 (t, 1H).

b) 2,6-dichlorobenzenesulfonamide

A solution of 2,6-dichlorobenzenesulfonyl chloride (10.50 g, 42.77 mmol) in 100 mL of pyridine was added into 100 mL of pyridine dropwise while anhydrous ammonia gas was passing through the solution simultaneously for 4 hours at 0° C. The mixture was acidified to pH>1 with 6N aq. HCl, then extracted with ethyl acetate. The combined organic layer was then dried ($Na_2SO_4$) and concentrated to give the desired product (8.69 g, 90%). EI-MS (m/z) 225.0, 227.1 (M$^-$).

c) 2,6-dichloro-3-nitrobenzenesulfonamide

Into a solution of 2,6-dichlorobenzenesulfonamide (7.8 g, 34.5 mmol) in 30 mL of concentrated sulfuric acid at 0°, nitric acid (1.74 mL, 41.4 mmol) was added dropwise. The mixture was stirred at 0° C. for 2 hours, then 200 mL of water was added to produce a precipitate. The resulting mixture was filtered. The white solid was collected, washed with water and dried in vacuo to give the desired product (7.17 g, 76%). $^1$H NMR (DMSO-d$_6$):δ8.25 (s, 2H), 8.20 (d, 1H), 7.92 (d, 1H).

d) 2-acetoxy-3-nitro-6-chlorobenzesulfonamide

A solution of 2,6-dichloro-3-nitrobenzenesulfonamide (2.04 g, 7.5 mmol), potassium acetate (2.21 g, 22.5 mmol) and 18-crown-6 (5.95 g, 22.5 mmol) in 50 mL of dimethyl sulfoxide was heated to 45° C. for 7 days. The mixture was acidified with 1N aq. HCl, and extracted with ethyl acetate. The organic layer was concentrated to give the crude. Column chromatography on silica gel, eluting with ethyl acetate/hexane/acetic acid (50/49/1, v/v/v), gave the desired product (1.67 g, 76%). EI-MS (m/z) 293.1, 295.1 (M$^-$).

e) 2-hydroxy-3-nitro-6-chlorobenzesulfonamide

A solution of 2-acetoxy-3-nitro-6-chlorobenzenesulfonamide (1.72 g, 5.83 mmol), chlorotrimethylsilane (2 mL) and fuming sulfuric acid (0.5 mL) in methanol was heated to reflux for 20 hours. The solvent was evaporated. The residue was diluted with ethyl acetate and washed with water. The organic layer was then dried (Na$_2$SO$_4$) and concentrated to give the desired product (1.0 g, 68%). EI-MS (m/z) 251.1, 253.2 (M$^-$).

f) 2-hydroxy-3-amino-6-chlorobenzene sulfonamide

To a solution of 2-hydroxy-3-nitro-6-chlorobenzenesulfonamide (1.1 g, 4.36 mmol) in ethyl acetate, was added 10% Pd/C (500 mg). The mixture was flushed with hydrogen, and then stirred under a hydrogen atmosphere at balloon pressure for 4 hours at room temperature. The mixture was filtered through celite and the celite was washed with methanol. The solvent was evaporated to give the desired product (91%). EI-MS (m/z) 221.1, 223.1 (M$^-$).

Example 1

Standard Procedure for the Condensation of Anilines with Isocyanates. Preparation of N-allyl-N'-(3-aminosulfonyl-4-chloro-2-hydroxyphenyl)urea A solution of 3-amino-6-chloro-2-hydroxybenzenesulfonamide (40 mg, 0.18 mmol) and allyl isocyanate (19 μL, 0.22 mmol) in 1 mL of N,N-dimethyl-formamide was stirred at room temperature for 20 hours. The mixture was diluted with ethyl acetate and washed with water to give the crude. Purification upon column chromatograph on silica gel, eluting with ethyl acetate/hexane (70/30, v/v), gave the desired product (15 mg, 27%). EI-MS (m/z) 304.1, 306.4 (M$^-$).

Example 2

Preparation of N-(3-aminosulfonyl-4-chloro-2-hydroxyphenyl)-N'-isopropylurea

A solution of 3-amino-6-chloro-2-hydroxybenzenesulfonamide (150 mg, 0.67 mmol) and isopropyl isocyanate (80 μL, 0.81 mmol) in 1 mL of N,N-dimethyl-formamide was stirred at room temperature for 20 hours. The mixture was diluted with ethyl acetate and washed with water to give the crude. Purification upon column chromatograph on silica gel, eluting with ethyl acetate/hexane (50/50, v/v), followed by recrystallization from acetone and hexane, gave the desired product (111 mg, 54%). LC-MS (m/z) 308.0 (M$^+$).

Example 3

Preparation of N-(3-aminosulfonyl-4-chloro-2-hydroxyphenyl)-N'-ethylurea

A solution of 3-amino-6-chloro-2-hydroxybenzenesulfonamide (150 mg, 0.67 mmol) and ethyl isocyanate (64 μL, 0.81 mmol) in 1 mL of N,N-dimethyl-formamide was stirred at room temperature for 20 hours. The mixture was diluted with ethyl acetate and washed with water to give the crude. Purification upon column chromatograph on silica gel, eluting with ethyl acetate/hexane (50/50, v/v), followed by recrystallization from acetone and hexane, gave the desired product (88 mg, 44%). LC-MS (m/z) 294.0 (M$^+$).

Example 4

Preparation of N-(3-aminosulfonyl-4-chloro-2-hydroxyphenyl)-N'-propylurea

A solution of 3-amino-6-chloro-2-hydroxybenzenesulfonamide (150 mg, 0.67 mmol) and propyl isocyanate (76 μL, 0.81 mmol) in 1 mL of N,N-dimethyl-formamide was stirred at room temperature for 20 hours. The mixture was diluted with ethyl acetate and washed with water to give the crude. Purification upon column chromatograph on silica gel, eluting with ethyl acetate/hexane (50/50, v/v), followed by recrystallization from acetone and hexane, gave the desired product (92 mg, 44%). LC-MS (m/z) 308.2 (M$^+$).

Example 5

Preparation of N-(3-aminosulfonyl-4-chloro-2-hydroxyphenyl)-N'-(ethoxycarbonyl)methylurea A solution of 3-amino-6-chloro-2-hydroxybenzenesulfonamide (170 mg, 0.76 mmol) and ethyl isocyanatoacetate (103 μL, 0.92 mmol) in 1.5 mL of N,N-dimethyl-formamide was stirred at room temperature for 20 hours. The mixture was diluted with ethyl acetate and washed with water to give the crude. Purification upon column chromatograph on silica gel, eluting with ethyl acetate/hexane (60/40, v/v), followed by Gilson HPLC separation, gave the desired product (20 mg, 7%). LC-MS (m/z) 352.0 (M$^+$).

Example 6

N-(3-aminosulfonyl-4-chloro-2-hydroxyphenyl)-N'-phenethyl urea

A solution of 3-amino-6-chloro-2-hydroxybenzenesulfonamide (120 mg, 0.54 mmol) and phenethyl isocyanate (82 μL, 0.59 mmol) in 1.0 mL of N,N-dimethyl-formamide was stirred at room temperature for 20 hours. Purification upon column chromatograph on silica gel, eluting with ethyl acetate/hexane (50/50, v/v), gave the desired product (109 mg, 55%). LC-MS (m/z) 369.8 (M$^+$).

Example 7

N-(3-aminosulfonyl-4-chloro-2-hydroxyphenyl)-N'-sec-butyl urea

A solution of 3-amino-6-chloro-2-hydroxybenzenesulfonamide (200 mg, 0.90 mmol) and sec-butyl isocyanate (102 μL, 0.90 mmol) in 1.5 mL of N,N-dimethyl-formamide was stirred at room temperature for 20 hours. Purification upon column chromatograph on silica gel, eluting with ethyl acetate/hexane (40/60, v/v), gave the desired product (156 mg, 54%). LC-MS 322.2 (M$^+$).

Example 8

Standard Procedure for the Synthesis of Ureas by Coupling Carboxylic Acids with an Aniline. Synthesis of 6-Chloro-3-[3-(1-ethyl-propyl)-ureido]-2-hydroxy-benzenesulfonamide To a solution of 2-ethylbutyric acid (0.125 mL, 1.0 mmol) in DMF (0.5 mL) was added DPPA (0.25 mL, 1.2 mmol) and TEA (0.25 mL, 1.8 mmol) and the reaction heated at 70° C. After 18 hrs, 3-Amino-6-chloro-2-hydroxy-benzenesulfonamide (1.0 mmol) was added and the reaction heated at 70° C. After 18 hrs, the reaction mixture was quenched with water and extracted with ethyl acetate. The organic layers were dried over anhydrous magnesium sulfate, and concentraed under reduced pressure. The crude residue was purified via HPLC to give 51 mg (15%) of 6-Chloro-3-[3-(1-ethyl-propyl)-ureido]-2-hydroxy-benzenesulfonamide. LC-MS (m/z) 336 (M$^+$).

Example 9

Synthesis of N-(3-aminosulfonyl-4-chloro-2-hydroxyphenyl)-N'-2-methylpentanyl urea 2-azidocarbonylpentane Under Ar, a mixture of azidotrimethylsilane (1.15 g, 9.98 mmol) and chromic anhydride (998 mg, 9.98 mmol) was stirred at room temperature till homogeneous solution. The solution of 2-methylpentanal (500 mg, 4.99 mmol) in 5 mL of dichloromethane was added. The mixture was stirred another 5 hours, and then filtered through silica gel. The filtrate was concentrated to give the crude material. FT-IR 2135.80 cm$^{-1}$, 2110.9 cm$^{-1}$.

N-(3-aminosulfonyl-4-chloro-2-hydroxyphenyl)-N'-2-methylpentanyl urea

A solution of 3-amino-6-chloro-2-hydroxybenzenesulfonamide (175 mg, 0.78 mmol) and the crude 2-azidocarbonyl pentane in 2 mL of N,N-dimethyl-formamide was stirred at room temperature for 20 hours. Purification upon Gilson HPLC, eluting with acetonitrile/water (10/90, v/v to 90/10, v/v, over 10 min), gave the desired product (5 mg, 2%). LC-MS (m/z) 336.2 (M$^+$).

Example 10

N-(3-aminosulfonyl-4-chloro-2-hydroxyphenyl)-N'-(isoleucine-methyl ester) urea

A solution of 3-amino-6-chloro-2-hydroxybenzenesulfonamide (400 mg, 1.80 mmol) and (2s, 3s)-2-isocyanato-3-methylvaleric acid methyl ester (338 mg, 1.98 mmol) in 1.5 mL of N,N-dimethyl-formamide was stirred at room temperature for 20 hours. Purification upon column chromatograph on silica gel, eluting with ethyl acetate/hexane/AcOH (60/40/1, v/v/v), followed by Gilson HPLC separation, gave the desired product (20 mg, 28%). LC-MS (m/z) 394.2 (M$^+$).

Example 11

N-(3-aminosulfonyl-4-chloro-2-hydroxyphenyl)-N'-isoleucine urea

A solution of N-(3-aminosulfonyl-4-chloro-2-hydroxyphenyl)-N'-(isoleucine-methyl ester)urea (80 mg, 0.20 mmol) and lithium hydroxide (40 mg, 1.67 mmol) in methanol was heated to reflux for 18 hours. Purification upon Gilson HPLC, eluting with acetonitrile (0.1% TFA)/water (0.1% TFA) (10/90, v/v to 90/10, v/v, over 10 min), gave the desired product (42 mg, 55%). LC-MS (m/z) 380.0 (M$^+$).

METHOD OF TREATMENT

The compounds of Formula (I), or a pharmaceutically acceptable salt thereof can be used in the manufacture of a medicine for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

The compounds of Formula (I), in generally have been shown to have a longer t½ and improved oral bioavailabilty over the compounds disclosed in WO 96/25157 and WO 97/29743 whose disclosures are incorporated herein by reference.

There are many disease states in which excessive or unregulated IL-8 production is implicated in exacerbating and/or causing the disease. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, multiple sclerosis, endotoxic shock, gram negative sepsis, toxic shock syndrome, cardiac and renal reperfusion injury, glomerulonephritis, thrombosis, graft vs. host reaction, Alzheimer's disease, allograft rejections, malaria, restenosis, angiogenesis, atherosclerosis, osteoporosis, gingivitis and undesired hematopoietic stem cells release and diseases caused by respiratory viruses, herpes viruses, and hepatitis viruses, meningitis, cystic fibrosis, pre-term labor, cough, pruritus, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, uveitis, polymyositis, vasculitis, acne, gastric and duodenal ulcers, celiac disease, esophagitis, glossitis, airflow obstruction, airway hyperresponsiveness, bronchiolitis obliterans organizing pneumonia, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertropy, sarcoidosis, small airway disease, ventilation-perfusion mismatching, wheeze, colds and lupus.

These diseases are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ, NAP-2 or ENA-78 have the unique property of promoting neutrophil chemotaxis, enzyme release including but not limited to elastase release as well as superoxide production and activation. The α-chemokines but particularly, GROα, GROβ, GROγ, NAP-2 or ENA-78, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., *Nature* 381, pp. 661 (1996) and Koup et al., *Nature* 381, pp. 667 (1996).

Present evidence also indicates the use of IL-8 inhibitors in the treatment of atherosclerosis. The first reference, Boisvert et al., *J. Clin. Invest*, 1998, 101:353–363 shows, through bone marrow transplantation, that the absence of IL-8 receptors on stem cells (and, therefore, on monocytes/macrophages) leads to a reduction in the development of atherosclerotic plaques in LDL receptor deficient mice. Additional supporting references are: Apostolopoulos, et al., *Arterioscler. Thromb. Vase. Biol.* 1996, 16:1007–1012; Liu, et al., *Arterioscler. Thromb. Vasc. Biol*, 1997, 17:317–323; Rus, et al., *Atherosclerosis.* 1996, 127:263–271.; Wang et al., *J. Biol. Chem.* 1996, 271:8837–8842; Yue, et al., *Eur. J. Pharmacol.* 1993, 240:81–84; Koch, et al., *Am. J. Pathol.*, 1993, 142:1423–1431.; Lee, et al., *Immunol. Lett.*, 1996, 53, 109–113.; and Terkeltaub et al., *Arterioscler. Thromb.*, 1994, 14:47–53.

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., *Stroke*, Vol. 25., No. 7, pp. 1481–88 (1994) whose disclosure is incorporated herein by reference.

Models of closed head injuries and treatment with mixed 5-LO/CO agents is discussed in Shohami et al., *J. of Vaisc & Clinical Physiology and Pharmacology*, Vol. 3, No. 2, pp. 99–107 (1992) whose disclosure is incorporated herein by reference. Treatment, which reduced edema formation, was found to improve functional outcome in those animals treated.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease state mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule, which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GRO-α, GRO-β, GRO-γ, NAP-2, ENA-78, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I) the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples, which are merely illustrative and are not to be construed as a limitation of the scope of the present invention.

BIOLOGICAL EXAMPLES

The IL-8 and GRO-α chemokine inhibitory effects of compounds of the present invention are determined by the following in vitro assay:

Receptor Binding Assays:

[$^{125}$I] IL-8 (human recombinant) is obtained from Amersham Corp., Arlington Heights, Ill., with specific activity 2000 Ci/mmol. GRO-α is obtained from NEN—New England Nuclear. All other chemicals are of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J. Biol. Chem.*, 249 pp 2195–2205 (1974)). Except that the homogenization buffer is changed to 10 mM Tris-HCL, 1 mM MgSO$_4$, 0.5 mM EDTA (ethylenediaminetetra-acetic acid), 1 mM PMSF (α-toluenesulphonyl fluoride), 0.5 mg/L Leupeptin, pH 7.5. Membrane protein concentration is determined using Pierce Co. micro-assay kit using bovine serum albumin as a standard. All assays are performed in a 96-well micro plate format. Each reaction mixture contains $^{125}$I IL-8 (0.25 nM) or $^{125}$I GRO-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM Na and 0.03% CHAPS. In addition, drug or compound of interest is added which has been pre-dissolved in DMSO so as to reach a final concentration of between 0.01 nM and 100 uM. The assay is initiated by addition of $^{125}$I-IL-8. After 1 hour at room temperature the plate is harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter is then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

Representative compounds of Formula (I), Examples 1 to 106 have exhibited positive inhibitory activity in this assay at IC$_{50}$ levels<30 μM.

Chemotaxis Assay:

The in vitro inhibitory properties of these compounds are determined in the neutrophil chemotaxis assay as described in Current Protocols in Immunology, vol. I, Suppl 1, Unit 6.12.3., whose disclosure is incorporated herein by reference in its entirety. Neutrophils where isolated from human blood as described in Current Protocols in Immunology Vol. I, Suppl 1 Unit 7.23.1, whose disclosure is incorporated herein by reference in its entirety. The chemoattractants IL-8, GRO-α, GRO-β, GRO-γ and NAP-2 are placed in the bottom chamber of a 48 multiwell chamber (Neuro Probe, Cabin John, MD) at a concentration between 0.1 and 100 nM. The two chambers are separated by a 5 uM polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% CO$_2$. At the end of the incubation period, the polycarbonate membrane is removed and the topside washed, the membrane then stained using the Diff Quick staining protocol (Baxter Products, McGaw Park, Ill., USA). Cells, which have chemotaxed to the chemokine, are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay:

The compounds of this invention are tested for their ability to prevent Elastase release from human neutrophils. Neutrophils are isolated from human blood as described in Current Protocols in Immunology Vol. I, Suppl 1 Unit 7.23.1. PMNs 0.88×10$^6$ cells suspended in Ringer's Solution (NaCl 118, KCl 4.56, NaHCO$_3$ 25, KH$_2$PO$_4$ 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800xg 5 min.) and 100 ul of the supernatant removed. This supernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al *J. Biol. Chem.* 254 4027 (1979). The amount of Elastase released from the PMNs is calculated by measuring the rate of MeOSuc-Ala-Ala-Pro-Val-AMC degradation.

TNF-α in Traumatic Brain Injury Assay:

The present assay provides for examination of the expression of tumor necrosis factor mRNA in specific brain regions, which follow experimentally, induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA are isolated and Northern blot hybridization is performed and quantitated relative to an TNF-α positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (46±8%, p<0.05), LC (30±3%, p<0.01) and LA (32±3%, p<0.01) at 6 hr which resolves by 24 hr following injury. In the contralateral hemisphere, expression of TNF-α mRNA is increased in RH (46±2%, p<0.01), RC (4±3%) and RA (22±8%) at 1 hr and in RH (28±11%), RC (7±5%) and RA (26±6%, p<0.05) at 6 hr but not at 24 hr following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model for IL-1β mRNA:

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on the same gel. At 1 hr following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula (I):

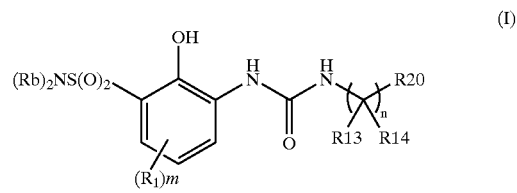

wherein $R_b$ is independently selected from the group consisting of hydrogen, $NR_6R_7$, OH, $OR_a$, $C_{1-5}$alkyl, aryl, aryl$C_{1-4}$ alkyl, aryl $C_{2-4}$alkeny,; cycloalkyl, cycloalkyl $C_{1-5}$alkyl, heteroaryl, heteroaryl$C_{1-4}$alkyl, heteroaryl$C_{2-4}$ alkenyl, heterocyclic, heterocyclic $C_{1-4}$alkyl, and a heterocyclic $C_{2-4}$alkenyl moiety, all of which moieties may be optionally substituted one to three times independently by halogen, nitro, halosubstituted $C_{1-4}$ alkyl, $C_{1-4}$ alkyl, amino, mono or di-$C_{1-4}$ alkyl substituted amine, $OR_a$, $C(O)R_a$, $NR_aC(O)OR_a$, $OC(O)NR_6R_7$, hydroxy, $NR_9C(O)R_a$, $S(O)_{m'}R_a$, $C(O)NR_6R_7$, $C(O)OH$, $C(O)OR_a$, $S(O)_2NR_6R_7$, and $NHS(O)_2R_a$, alternatively, the two $R_b$ substituents can join to form a 3–10 membered ring, optionally substituted and containing, in addition to carbon, independently, 1 to 3 moieties selected from the group consisting of $NR_a$, O, S, SO, and $SO_2$ which can be optionally unsaturated;

$R_a$ is selected from the group consisting of alkyl, aryl, aryl$C_{1-4}$alkyl, heteroaryl, heteroaryl $C_{1-4}$alkyl, heterocyclic, $COOR_a$, and a heterocyclic $C_{1-4}$alkyl moiety, all of which moieties may be optionally substituted;

m is an integer having a value of 1 to 3;

m' is 0, or an integer having a value of 1 or 2;

n is an integer having a value of 1 to 5;

q is 0, or an integer having a value of 1 to 10;

t is 0, or an integer having a value of 1 or 2;

s is an integer having a value of 1 to 3;

$R_1$ is independently selected from the group consisting of hydrogen, halogen, nitro, cyano, $C_{1-10}$ alkyl, halosubstituted $C_{1-10}$ alkyl, $C_{2-10}$ alkenyl, $C_{1-10}$ alkoxy, halosubstituted $C_{1-10}$alkoxy, azide, $S(O)_tR_4$, $(CR_8R_8)_qS(O)_tR_4$, hydroxy, hydroxy substituted $C_{1-4}$alkyl, aryl, aryl $C_{1-4}$ alkyl, aryl $C_{2-10}$ alkenyl, aryloxy, aryl $C_{1-4}$ alkyloxy, heteroaryl, heteroarylalkyl, heteroaryl $C_{2-10}$ alkenyl, heteroaryl $C_{1-4}$ alkyloxy, heterocyclic, heterocyclic $C_{1-4}$alkyl, heterocyclic$C_{1-4}$alkyloxy, heterocyclic$C_{2-10}$ alkenyl, $(CR_8R_8)_q NR_4R_5$, $(GR_8R_8)_q C(O)NR_4R_5$, $C_{2-10}$ alkenyl $C(O)NR_4R_5$, $(CR_8R_8)_q C(O)NR_4R_{10}$, $S(O)_3R_8$, $(CR_8R_8)_q C(O)R_{11}$, $C_{2-10}$ alkenyl $C(O)R_{11}$, $C_{2-10}$ alkenyl $C(O)OR_{11}$, $(CR_8R_8)_q C(O)OR_{11}$, $(CR_8R_8)_q OC(O)R_{11}$, $(CR_8R_8)_q NR_4C(O)R_{11}$, $(CR_8R_8)_q C(NR_4)NR_4R_5$,$(CR_8R_8)_q NR_4C(NR_5)$ $R_{11}$, $(CR_8R_8)q$ $NHS(O)_2R_a$, and $(CR_8R_8)q$ $S(O)_2NR_4R_5$; or two $R_1$ moieties together may form $O-(CH_2)_sO$ or a 5 to 6 membered saturated or unsaturated ring, wherein the alkyl, aryl, arylalkyl, heteroaryl, heterocyclic moieties may be optionally substituted;

$R_4$ and $R_5$ are, independently, selected form the group consisting of hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, and heterocyclicC $_{1-4}$ alkyl; or $R_4$ and $R_5$ together with the nitrogen to which they are attached form a 5 to 7 member ring which may optionally comprise an additional heteroatom selected from O, N and S;

$R_6$ and $R_7$ are independently selected from the group consisting of hydrogen, $C_{1-4}$ alkyl, heteroaryl, aryl, aklyl aryl, and alkyl $_{1-4}$ heteroalkyl; or $R_6$ and $R_7$ together with the nitrogen to which they are attached form a 5 to 7 member ring which ring may optionally contain an additional heteroatom is selected from oxygen, nitrogen and sulfur, which ring may be optionally substituted;

$R_8$ is hydrogen or $C_{14}$ alkyl;

$R_9$ is a $C_{1-4}$alkyl;

$R_{10}$ is $C_{1-10}$ alkyl $C(O)_2R_8$;

$R_{11}$ is selected from the group consisting of hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, and optionally substituted heterocyclic$C_{1-4}$ alkyl; and $R_{13}$ and $R_{14}$ are independently selected from the group consisting of hydrogen, optionally substituted $C_{1-4}$ alkyl, optionally substituted $C_{1-4}$ alkenyl, optionally substituted $C_4$ alkenyl optionally substituted heteroaryl, optionally substituted heteroaryl $C_{1-4}$ alkyl, optionally substituted heterocyclic, optionally substituted heterocyclic$C_{1-4}$alkyl, halogen, nitro, $OR_a$, $NR_6R_7$, $C(O)R_a$, $NR_{11}$ $C(O)OR_a$, $OC(O)NR_6R_7$, $NR_{11}C(O)R_a$, $S(O)_mR_a$, $C(O)NR_6R_7$, $C(O)OH$, $C(O)OR_a$, $S(O)_2NR_6R_7$, and $NR_{11}S(O)_2R_a$; and $R_{20}$ is selected from the group consisting of hydrogen, alkyl, alkynyl, alkenyl, heterocyclic, and heteroaromatic all of which maybe optionally substituted;

or a pharmaceutically acceptable salt thereof.

2. The compound according to claim 1 wherein $R_1$ is substituted in the 4-position by an electron withdrawing moiety.

3. The compound according to claim 2 wherein $R_1$ is halogen, cyano or nitro.

4. The compound according to claim 3 wherein $R_1$ is halogen.

5. The compound according to claim 4 wherein $R_1$ is independently, fluorine, chlorine, or bromine.

6. The compound according to claim 1 wherein $R_b$ is hydrogen, $C_{1-4}$ alkyl, or $C_{1-4}$ alkyl substituted with $C(O)OH$, or $C(O)OR_a$.

7. The compound according to claim 1 which is selected from the group consisting of:

N-allyl-N'-(3-aminosulfonyl-4-chloro-2-hydroxyphenyl) urea;

N-(3-aminosulfonyl-4-chloro-2-hydroxyphenyl)-N'-isopropylurea;

N-(3-aminosulfonyl-4-chloro-2-hydroxyphenyl)-N'-ethylurea;

N-(3-aminosulfonyl-4-chloro-2-hydroxyphenyl)-N'-propylurea; and

N-(3-aminosulfonyl-4-chloro-2-hydroxyphenyl)-N'-(ethoxycarbonyl)methylurea;

6-Chloro-2-hydroxy-3-(3-phenethyl-ureido)-benzenesulfonamide;

3-(3-sec-Butyl-ureido)-6-chloro-2-hydroxy-benzenesulfonamide;

6-Chloro-3-[3-(1-ethyl-propyl)-ureido]-2-hydroxy-benzenesulfonamide;

6-Chloro-2-hydroxy-3-[3-(1-methyl-butyl)-ureido]-benzenesulfonamide;

(2S,3S)-2-[3-(4-Chloro-2-hydroxy-3-sulfamoyl-phenyl)-ureido]-3-methyl-pentanoic acid methyl ester; and (S)-2-[3-(4-Chloro-2-hydroxy-3-sulfamoyl-phenyl)-ureido]-3-methyl-pentanoic acid.

8. A compound according to claim 7 selected from the group consisting of N-allyl-N'-(3-aminosulfonyl-4-chloro-2-hydroxyphenyl)urea; and N-(3-aminosulfonyl-4-chloro-2-hydroxyphenyl)-N'-isopropylurea.

9. A compound according to claim 7 wherein the compound is in its sodium salt form.

10. A compound according to claim 7 wherein the compound is in its potassium salt form.

11. A pharmaceutical composition comprising a compound according to claim 1 and a pharmaceutically acceptable carrier or diluent.

12. A method of treating a chemokine mediated disease, wherein the chemokine binds to an IL-8 a or b receptor in a mammal, which method comprises administering to said mammal an effective amount of a compound of the formula according to claim 1.

13. The method according to claim 12 wherein the mammal is afflicted with a chemokine mediated disease selected from the group consisting of:

Psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, multiple sclerosis, endotoxic shock, grain negative sepsis, toxic shock syndrome, cardiac and renal reperfusion injury, glomerulonephritis, thrombosis, graft vs. host reaction, Alzheimer's disease, allograft rejections, malaria, restenosis, angiogenesis, atherosclerosis, osteoporosis, gingivitis and undesired hematopoietic stem cells release and diseases caused by respiratory viruses, herpes viruses, and hepatitis viruses, meningitis, cystic fibrosis, pre-term labor, cough, pruritus, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, uveitis, polymyositis, vasculitis, acne, gastric and duodenal ulcers, celiac disease, esophagitis, glossitis, airflow obstruction, airway hyperresponsiveness, bronchiolitis obliterans organizing pneumonia, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertropy, sarcoidosis, small airway disease, ventilation-perfusion mismatching, wheeze, colds and lupus.

* * * * *